(12) United States Patent
Wild

(10) Patent No.: US 7,916,297 B2
(45) Date of Patent: Mar. 29, 2011

(54) METHOD AND APPARATUS FOR TESTING A TEST OBJECT

(75) Inventor: Michael Wild, Deggendorf (DE)

(73) Assignee: Ullrich GmbH, Zwiesel (DE)

( * ) Notice: Subject to any disclaimer, the term of this patent is extended or adjusted under 35 U.S.C. 154(b) by 330 days.

(21) Appl. No.: 12/195,693

(22) Filed: Aug. 21, 2008

(65) Prior Publication Data

US 2009/0051919 A1 Feb. 26, 2009

(30) Foreign Application Priority Data

Aug. 22, 2007 (DE) .......................... 10 2007 039 630

(51) Int. Cl.
*G01N 21/00* (2006.01)
(52) U.S. Cl. ...... 356/432; 356/399; 356/244; 356/239.4
(58) Field of Classification Search .................. 356/399, 356/432, 512, 51, 521, 124, 128, 244, 239.1, 356/237.1, 239.4
See application file for complete search history.

(56) References Cited

U.S. PATENT DOCUMENTS

| 4,049,350 | A | 9/1977 | Briick |
| 4,232,966 | A | 11/1980 | Schpak et al. |
| 7,119,884 | B2 * | 10/2006 | Ottens et al. ................... 355/72 |

FOREIGN PATENT DOCUMENTS

| DE | 8714912.5 | 11/1987 |
| DE | 19631163 | 8/1996 |
| DE | 102005033013 | 1/2007 |
| WO | 2007/023042 | 3/2007 |

OTHER PUBLICATIONS

G. Zeidler. "Optical Fiber Elastomeric (EOF)" *Film Collection, Optical Fibers, Elastomers.* 17 pages (Mar. 26, 2003).

* cited by examiner

*Primary Examiner* — Gregory J Toatley
*Assistant Examiner* — Iyabo S Alli
(74) *Attorney, Agent, or Firm* — Occhiuti Rohlicek & Tsao LLP

(57) ABSTRACT

A method of testing a test object, comprising the steps of arranging the test object at a deformable contact element of a holding device, wherein the contact element is at least partially deformed so that at least a partial area of the test object is in gap-free contact with at least a partial area of the contact element, and wherein for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical; having the electromagnetic radiation radiate through the holding device and the test object in parallel to the predefined through-radiation direction detecting the electromagnetic radiation after through-radiation; and evaluating the detected electromagnetic radiation.

20 Claims, 1 Drawing Sheet

METHOD AND APPARATUS FOR TESTING A TEST OBJECT

CROSS-REFERENCE TO RELATED APPLICATIONS

This application claims the priority of German Application No. 102007039630.0, filed on Aug. 22, 2007. The contents of the application are hereby incorporated by reference in their entirety.

FIELD OF THE INVENTION

The present invention relates to a method of testing a test object and an apparatus for testing a test object.

BACKGROUND OF THE INVENTION

Conventionally, a so-called semi-finished glass product that can be processed further is manufactured. Such a semi-finished product is referred to as a "gob", for example. A gob may e.g. have a substantially frustoconical shape. For further processing, a gob may undergo blank pressing, and a lens, a bottle or another glass object can be produced therefrom. For manufacturing reasons, outer surfaces of a gob may be substantially blank, transparent and bright. Conventionally, the outer surfaces are corrugated though. Particularly, a peripheral surface of the gob may be very corrugated.

If the gobs are further processed to form optical lenses for example, the demands on the gobs with respect to stains, bubbles, stones, and striae are very high. For this reason, the gobs are usually sorted manually and are systematically resorted if the number of critical blemishes and complaints increases. However, due to the high number of pieces involved in manufacturing and the difficult recognizability of defects, such as bubbles up to 0.2 mm and/or stones up to 0.05 mm, a visual inspection is limited.

Further difficulties in the visual inspection result e.g. from the distortion of the image of the gob and the defects contained therein, which difficulties are caused by the corrugation of the surface. In order to avoid the distortion, gobs with an almost identical refractive index are conventionally tested by immersion in liquid. However, owing to the required gob cleaning and drying, the liquid immersion is not practicable for testing several thousand gobs per day.

SUMMARY OF THE INVENTION

It is therefore an object of the present invention to provide a possibility for an easy and fast testing of a test object. This object is solved by the method according to claim 1 and the apparatus according to claim 7. Preferred embodiments and variants are the subject of the dependent claims.

An aspect of the present invention relates to a method of testing a test object, comprising the steps of:
  arranging the test object at a deformable contact element of a holding device,
  wherein the contact element is at least partially deformed so that at least a partial area of the test object is in gap-free contact with at least a partial area of the contact element, and
  wherein for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical;
  having the electromagnetic radiation radiate through the holding device and the test object in parallel to the predefined through-radiation direction;
  detecting the electromagnetic radiation after through-radiation; and
  evaluating the detected electromagnetic radiation.

Advantageously, an optical testing of one or more bodies, for example transparent bodies as preferred test objects, can be carried out in this way. Moreover, it is an advantage that it is not necessary for the test objects to have parallel and/or planar surfaces. Instead, the method allows for a simple and fast testing of test objects with non-plane-parallel sides and preferably little roughness, such as lenses, gobs, etc., in transmitted light as the preferred electromagnetic radiation. Here, a complex and expensive optical arrangement for compensation of the curved surfaces and/or immersion of the test object in liquid is advantageously avoided. Therefore, an inspection of the glass with respect to imperfections and defects, such as stones, bubbles, striae, possible tensions, etc., can be carried out in a simple manner. Advantageously, reflections or scatterings, which are caused by the surface roughness of the test object, are reduced. For this reason, it is advantageously not necessary for the test object to have smooth surfaces. Due to the low-distortion through-radiation and the reduction of reflection and scattering effects by means of the substantially identical optical path lengths of the electromagnetic radiation through the holding device and the test object, a low-distortion imaging of defects in the interior of the test body is possible. Advantageously, the detection limit for the spatial extent of imperfections or defects is reduced.

Consequently, the testing of undefinedly formed test objects, such as glass bodies, can advantageously be carried out automatically, wherein the method may particularly be employed for large numbers of pieces as well.

The term "gap-free" as defined by the present invention may be understood to be synonymous with "form-fitting". In other words, no further material, particularly no material whose refractive index is different from the refractive index of the contact element, is present between the contact element and the partial area of the test object, which is irradiated with the electromagnetic radiation.

Furthermore, the term "optical path length" may be understood to refer to the path on which the electromagnetic radiation passes through the contact element and the test object. The optical path length is substantially identical for at least two different paths on which the electromagnetic radiation passes through the contact element and the test object. In other words, the electromagnetic radiation can pass through a higher volume portion of the test object on a first path than on a second path. Similarly, the electromagnetic radiation can pass through a higher volume portion of the contact element on the second path than on the first path. However, the contact element is chosen such that the entire optical path length (i.e. the common optical path length through the contact element and the test object) on the first path is substantially identical with the entire optical path length (the common optical path length through the contact element and the test object) on the second path. In other words, there is a minor change in the refractive index ($\Delta n < 0.02$, preferably $\Delta n < 0.002$) upon transition from the contact element into the test object. In particular, this is achieved in that the deformable contact element compensates for the uneven shape of the test object by means of the gap-free arrangement of the test object on the contact element. In other words, the surface roughness of the test object is compensated for by the contact element.

The gap-free arrangement may also apply to several points, e.g. 3, 4, 5, 10, 15, 25, 50, etc., in particular to an entire partial area of the contact element at which the contact element contacts the test object. Consequently, the optical path length through the contact element and the test object for parallel electromagnetic radiation, which passes through the contact element, the contact surface and the test object, is preferably substantially identical for all points of the contact surface that contact the test object.

The optical path length may also change due to impurities and/or striae, etc. in the test object. In this case, the optical path length of the first optical path may be different from that of the second optical path. However, this difference is preferably detected by evaluating the detected electromagnetic radiation, and thus the impurity, or impurities, and/or stria(e), etc., can be located. Therefore, in the ideal case, a substantially identical optical path length for the first and second optical paths only exists for test objects that have no impurities, striae, etc., i.e. for substantially homogenous test objects. This applies in particular to fully homogenous test objects.

Moreover, the through-radiation direction may be defined substantially arbitrarily. The through-radiation direction is in particular perpendicular to the direction of the electric field and to the direction of the magnetic field of the electromagnetic radiation.

As defined by the present invention, the terms "substantially identical" and "almost identical" imply fully identical or with little deviation from an identical optical path length. For example, a deviation of 1%, 2%, 5%, or 10% is possible. The deviation may also be in the order of magnitude of the measuring accuracy of the optical path.

The term "complementary" as defined by the present invention implies "completing the other". For example, the complementary contact elements can contact the test object at opposite surfaces. The contact element and the complementary contact element may particularly be opposite to each other.

Preferably, the method comprises the further step of:
arranging the test object at a deformable complementary contact element of a complementary holding device, wherein the complementary contact element is at least partially deformed so that at least a complementary partial area of the test object is in gap-free contact with at least a complementary partial area of the complementary contact element, wherein for at least two contact points of the contact element and/or the complementary contact element, which are in contact with the partial area of the test object and/or the complementary partial area of the test object, upon through-radiation by means of electromagnetic radiation that is parallel to a predefined through-radiation direction, an optical path length of the electromagnetic radiation through the holding device, the test object and the complementary holding device is substantially identical; and wherein upon having the electromagnetic radiation radiate through the holding device and the test object, the complementary holding device is radiated through as well.

The above explanations analogously apply to a combination of the contact element, the test object and the complementary contact element. The above explanations with respect to the contact element analogously apply in particular to the complementary contact element.

Preferably, the method comprises the initial step of:
selecting the contact element and/or the complementary contact element with an optical refractive index that is substantially equal to the optical refractive index of the test object.

In other words, the electromagnetic radiation can radiate through the contact element(s) and the test object at least in the areas of gap-free arrangement of the contact element(s) and the test object, wherein due to the substantially identical refractive index in the contact element and the test object, the parallel radiation radiates through volume areas of substantially constant refractive index. The contact element(s) and the test object therefore appear as a uniform body in these areas. A deviation of the refractive index of the contact element and the test object of 20% to approx. 10%, preferably approx. 5%, more preferably 1%, is possible.

Furthermore, the electromagnetic radiation is preferably detected by means of an image-forming device.

The image-forming device may e.g. be a CCD chip, a digital camera, an optical sensor, an interferometer, etc. In particular, the image-forming device can enable an automatic, electronic image processing also at places of greater surface curvature. To this end, known electronic image-processing methods and apparatuses may be used for evaluation. Among others, classical detection methods for glass blemishes, such as they are described in Jebsen-Marwedel "Glastechnische Fabrikationsfehler", Springer 1980, may be used.

More preferably, the detected electromagnetic radiation is automatically examined and evaluated by means of an image-processing method.

Furthermore, the electromagnetic radiation is preferably homogeneous light, wherein inhomogeneity in the detected electromagnetic radiation is detected by means of the image-processing method.

A further aspect of the present invention relates to an apparatus for holding at least one test object, comprising
a holding device with at least one deformable contact element, wherein
a test object can be arranged at the deformable contact element such that
at least a partial area of the contact element can be brought into contact with at least a partial area of the test object in substantially gap-free fashion, and
for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical.

In other words, a further aspect of the present invention relates to an apparatus for holding at least one test object, comprising
a holding device with at least one deformable contact element, wherein
a test object is adapted to be arranged at the deformable contact element such that
at least a partial area of the contact element is adapted to be brought into contact with at least a partial area of the test object in substantially gap-free fashion, and
for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical.

Preferably, the apparatus comprises a complementary holding device with at least one deformable complementary contact element, wherein at least a complementary partial area of the test object can be brought into contact with at least a complementary partial area of the complementary contact element in substantially gap-free fashion.

Moreover, the deformable contact element and/or the complementary deformable contact element preferably has/have an optical refractive index that is substantially equal to an optical refractive index of the test object. Specifically, the contact element and/or the complementary contact element may be chosen such that the contact element and/or the complementary contact element has/have an optical refractive index that is substantially equal to an optical refractive index of the test object.

More preferably, the test object can be arranged at least partially between the contact element and the complementary contact element. In other words, the test object is adapted to be arranged at least partially between the contact element and the complementary contact element.

According to another preferred embodiment, the holding device comprises a base device at which the deformable contact element is arranged.

According to another preferred embodiment, the complementary holding device comprises a complementary base device at which the deformable complementary contact element is arranged.

Specifically, the base device and the contact element may be integrally connected to each other or form a unit, or be in one piece or be composed of a uniform material.

More preferably, the base device and/or the complementary base device has/have plane-parallel surfaces.

In other words, the base device and/or the complementary base device may be plate-shaped. Specifically, the base devices may be arranged in parallel to each other.

More preferably, the contact element and/or the complementary contact element is/are composed of an elastomer.

The elastomer may be at least partly surrounded by a film. Preferably, the elastomer is completely surrounded by a film.

According to a further preferred embodiment, the contact element and/or the complementary contact element is/are composed of a liquid or a gel, which is provided in a bag formed of a film. In other words, two bags may be provided, namely, one that corresponds to the contact element and one that corresponds to the complementary contact element.

Here, preferably the gel or the liquid, the film and the test object have a substantially identical refractive index.

More preferably, the apparatus comprises a detection device configured to detect electromagnetic radiation after at least partial through-radiation of the contact element and at least partial through-radiation of the test object.

The detection device may for example be a camera that is connected to, or in contact with, the contact element and/or the base device. The detection device may also comprise a glass plate or glass surface in contact with the contact element (on the side opposing the test object). The detection device may for example comprise a camera lens that is connected to the base device and/or the contact element.

Furthermore, the apparatus preferably comprises an evaluating device configured to evaluate the detected electromagnetic radiation.

An evaluating device may for example include a microprocessor. The microprocessor may also be part of another device and, for example, exchange data with the detection device.

Preferably, the apparatus comprises a display device configured to present the detected electromagnetic radiation.

For example, the display device may be a monitor. The monitor may also be part of another device and, for example, exchange data with the apparatus.

BRIEF DESCRIPTION OF THE FIGURES

In the following, preferred embodiments of the present invention will be described by way of example with reference to the accompanying figures, in which.

DETAILED DESCRIPTION

Figure 1:
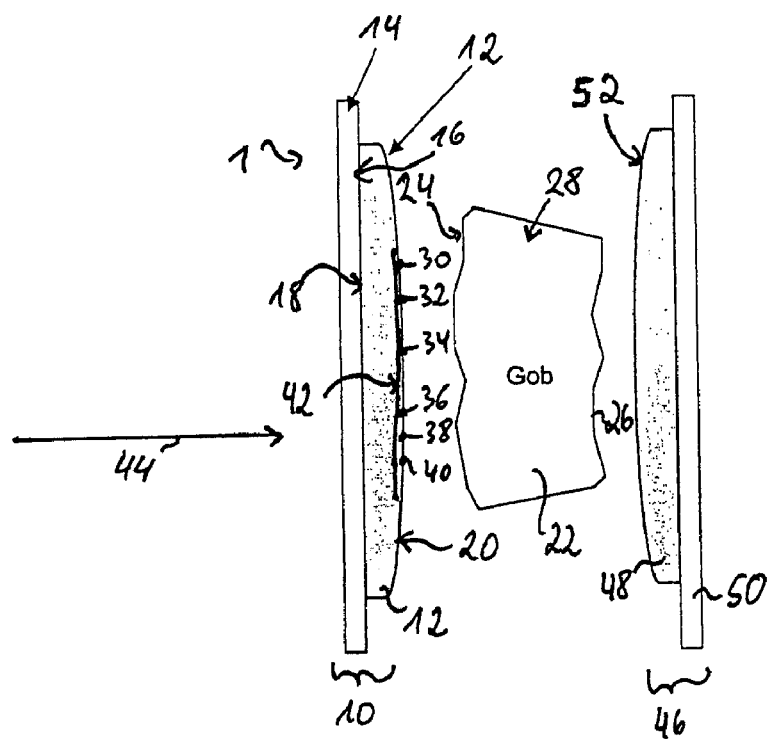
FIG. 1 is a schematic view of a preferred embodiment.

FIG. 1 shows an apparatus 1 comprising a holding device 10 and a contact element 12. The contact element 12 is exemplarily formed as a deformable elastomer and arranged at a base element 14. Preferably, the base element 14 has a plate-shaped design. The base element 14 may for example be a glass plate, an elastomer plate, or a plate composed of several materials. According to FIG. 1, the contact element 12 is arranged at the base element 14 in gap-free fashion. In other words, no further material, in particular no air or other gas, is present between a rear contact surface 16 of the contact element 12 and a contact surface 18 of the base element 14. Furthermore, there is no space between the contact surfaces 16, 18, i.e. there is no vacuum between the contact surfaces 16, 18 either.

Moreover, the contact element has a further, front contact surface 20. The front contact surface 20 is preferably provided opposite a test object 22. The test object 22 is, for example, a so-called gob 22 (see above). For example, the gob 22 consists of glass and is substantially transparent in the visible spectral range, i.e. between approx. 400 nm and approx. 700 nm. The gob 22 may be colored, e.g. blue, red, green, yellow, etc. Alternatively or in addition, the test object 22, or the gob 22, may also be at least partially transparent for electromagnetic radiation outside the visible spectral range. For example, the test object 22 may be at least partially transparent in the infrared range, particularly in the near and/or far infrared range, and/or in the UV range, and/or in the microwave range, etc. It is also possible for the test object to be opaque or only transparent to a limited extent in the visible spectral range (visible to the human eye) and to be at least partially transparent in one or more of the above-listed spectral ranges, or vice versa.

The term "at least partially transparent" as defined by the present invention implies that the test object is approx. 100%, or between approx. 70% and approx. 100%, preferably between approx. 80% and approx. 100% permeable, in particular approx. 95% permeable, or approx. 90%, approx. 85%, approx. 80%, approx. 75%, approx. 70%, approx. 50%, approx. 25% or approx. 10% permeable for electromagnetic radiation.

The test object 22 may e.g. have a frustoconical shape. To this end, the test object 22 comprises three surfaces, i.e. a front surface 24, a rear surface 26 as preferred complementary surface, and a peripheral surface 28. According to FIG. 1, the test object 22, i.e. the gob 22, is arranged such that the front surface 24 of the gob 22 can contact the front contact surface 20 of the contact element 12. However, the gob 22 may also be arranged in a different manner. For example, the gob 22 may also be arranged in a turned fashion, so that the rear surface 26 contacts the contact element 12, or the peripheral surface 28 contacts the contact element 12.

For example, the front surface 24 of the gob 22 may have a diameter of approx. 40 mm to approx. 70 mm, more preferably approx. 50 mm to approx. 60 mm, most preferably approx. 55 mm.

Moreover, the rear surface 26 of the gob 22 may have a diameter of approx. 35 mm to approx. 65 mm, more preferably approx. 45 mm to approx. 55 mm, most preferably approx. 50 mm.

The height of the gob 22 may be between approx. 10 mm to approx. 40 mm, preferably between approx. 20 mm and approx. 30 mm, most preferably approx. 25 mm.

A first contact point 30, a second contact point 32, a third contact point 34, a fourth contact point 36, a fifth contact point 38 and a sixth contact point 40 are exemplarily shown in FIG. 1. The contact points 30-40 are merely exemplary. It is also possible to only have 2, 3, 4 or 5 contact points. Alternatively, there may be a number of further contact points. Most preferably, there do not exist individual contact points but a partial contact area 42, which is a partial area of the contact surface 20.

The contact points 30-40 and/or the partial contact area 42 are not physical components of the contact element 12. Instead, the contact points 30-40 and the partial contact area 42 represent geometrical areas of the contact surface 20. Specifically, the contact surface 20 contacts the front surface 24 of the gob 22 at least at the contact points 30-40 or the partial contact area 42.

Furthermore, FIG. 1 exemplarily illustrates a through-radiation direction 44 along which electromagnetic radiation (not shown) at least partially radiates through the holding device 10, i.e. the base element 14 and the contact element 12, as well as the gob 22. The optical through-radiation direction may be substantially perpendicular to the contact surface 16 and the contact surface 18.

Moreover, FIG. 1 shows a complementary holding device 46 comprising a complementary contact element 48 and a complementary base element 50 with a complementary contact surface 52. The complementary holding device 46 may be substantially identical with the holding device 10.

Figure 2:
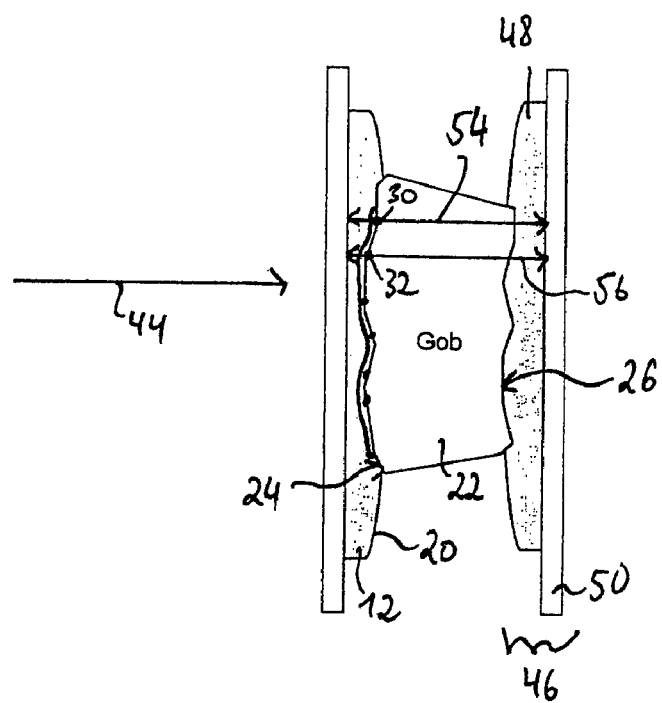
FIG. 2 is a further schematic view.

FIG. 2 shows the apparatus 1 of FIG. 1, however, with the test object 22 arranged both at the contact element 12 and the complementary contact element 48. The contact element 12 and/or the complementary contact element 48 may e.g. be cushions made of an elastomer. As illustrated in FIG. 2, the test object 22 is in contact with the contact element 12, wherein the contact element 12 is deformed due to the surface shape of the front surface 24 of the gob 22. Specifically, the front contact surface 20 of the contact element 12 is matched with the front surface 24 of the test object 22, i.e. the gob 22. This applies particularly to the contact points 30-40 or the partial contact area 42, at which the contact element 12, or rather the front contact surface 20 thereof, is in contact with the front surface 24 of the gob 22 in substantially gap-free fashion. Similarly, the complementary contact element 48 is in contact with the rear surface 26 (as preferred complementary surface) of the gob 22, wherein the complementary contact surface 52 of the complementary contact element 48 is deformed due to the surface shape of the rear surface 26 of the gob 22. The partial contact area is preferably identical to the front surface 24 if the gob 22 and the contact element 12, particularly the contact surfaces thereof, contact each other in gap-free fashion.

If electromagnetic radiation is radiated in parallel to the through-radiation direction 44, the optical path length of electromagnetic radiation along the path 54 through the contact point 30 is equal to the optical path length of electromagnetic radiation along the path 56 through the contact point 32. This is the case because the contact element 12, the gob 22 and the complementary contact element 48 have a substantially identical refractive index. Moreover, at the contact point 30 and the contact point 32, the contact surface 20 contacts the gob 22 in gap-free fashion, whereby there is no change of refractive index upon transition of the electromagnetic radiation from the contact element 12 into the gob 22. Optically speaking, the contact element 12 and the gob 22 behave as a uniform body. This applies to the contact point 32 as well. Furthermore, this also applies to the optical paths (not shown) at the further contact points 34-40 and the partial contact area 42. Analogously, this applies to the rear surface 26 of the gob 22 and the complementary contact element 48 as well.

As shown in FIG. 2, the optical path 54 extends through the contact element 12, the gob 22, and the complementary contact element 48. The optical path may also comprise the path through the base element 14 and the complementary base element 50. The same applies, by analogy, to the optical path 56.

In the case where e.g. the rear surface 26 of the gob 22 is a substantially planar surface, the complementary contact element 48 may be dispensed with. In this case, it may be sufficient to exclusively provide the holding device 10 and to bring the gob 22 into contact with the holding device 10. To this end, the contact with the contact element 12 may be such that the gob 22 is bound to the contact element 12. For example, the contact element 12 may have adhesive characteristics due to which the gob 22 adheres to the contact element 12.

Also, it is not necessary to provide the base element 14. Rather, for example the contact surface 18 of the contact element 12 may be formed such that it replaces the base element 14. Alternatively, the base element 14 and the contact element may be formed as one piece, in particular integrally. The base element 14 may also be a front surface of a lens or camera lens (not shown).

Thus, the apparatus 1 allows for an optical inspection using transmitted light, for example checking the image of the apparatus 1 with transmitted light (upon radiation of electromagnetic radiation in parallel to the through-radiation direction 44), and/or checking the absorption and/or checking scattering and/or checking the polarization by means of polarization optics. Advantageously, instead of immersion in liquid, the surface 24 and/or the surface 26 of the gob 22 is/are brought into contact with an index-matched, transparent, elastic polymer, for example silicone (as preferred embodiment of the contact element 12 and/or the complementary contact element 48). The refractive index of the gob may for example be approx. n=1.522. This value can be achieved by means of silicone elastomers, as e.g. described on a data sheet by the company Dow Corning with respect to silicone elastomers for a product with the designation JRC 6175.

The corrugation of the front surface 24 and/or the rear surface 26 of the gob 22, strongly exaggerated in FIG. 2, is compensated for by the elastomer in gap-free fashion, so that preferably the optical path length is almost identical at all points due to the configuration of glass plate 14—elastomer 12—gob 22—elastomer 48—glass plate 50. However, residual distortions resulting from the deformation of the elastomer are possible and may be taken into consideration upon evaluation.

Transmission through the configuration, i.e. the holding device 10, the test object 22 and the complementary holding device 46, may additionally be improved by an antireflection coating on one side each or both sides of the glass plates 14, 50.

In order to protect the elastomer 12, 48 from contamination, a thin film (not shown) or an antistick layer may be applied to the side 20, 52 that is in contact with the gob 22.

As an alternative to FIG. 2, the elastomer 12 may also be brought into contact with the peripheral surface 28. Upon contact at two diametrically opposed sides of the peripheral surface, an optical inspection may be carried out as well. Thus, striae in particular that are slightly below the front surface 24 and/or the rear surface 26 may be made visible.

Alternatively, instead of an elastomer 12, 48, a bag (not shown) made of a thin elastic film may be used, which is filled with a liquid or a gel matched with the refractive index of the glass body 22 as preferred test object 22. Ideally, the film is matched with the refractive index as well. By the viscous deformation of the liquid or the gel, substantially the same compensating effect is achieved at the surface as with the elastomer 12, 48. This embodiment is advantageous in that mechanical stresses, as may occur during deformation of the elastomer, are substantially absent from the liquid and the gel. Thus, stress-induced changes of the refractive index or stress birefringences, as may occur in the elastomer 12, 48, are substantially avoided using a gel or a liquid.

The apparatus 1 can be used for example, in conventional glass testing machines, wherein by use of camera technology with e.g. CCD and/or CMOS, an automated optical test by means of camera and image processing is possible. Bubbles in the test object may for example be recognized through the resulting scattered light.

The present invention is not limited to the previous description of preferred embodiments. Rather, the individual components of the previously described embodiment may be arbitrarily combined to form further embodiments. In particular, the electromagnetic radiation may be a homogeneous, rectified electromagnetic radiation. For example, the electromagnetic radiation may be polarised, in particular linearly or circularly polarised.

What is claimed is:

1. A method of testing a test object, comprising the steps of:
   arranging the test object at a deformable contact element of a holding device, wherein the contact element is at least partially deformed so that at least a partial area of the test object is in gap-free contact with at least a partial area of the contact element, and
   wherein for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical;
   having the electromagnetic radiation radiate through the holding device and the test object in parallel to the predefined through-radiation direction;
   detecting the electromagnetic radiation after through-radiation; and
   evaluating the detected electromagnetic radiation.

2. The method according to claim 1, comprising the further step of:
   arranging the test object at a deformable complementary contact element of a complementary holding device, wherein the complementary contact element is at least partially deformed so that at least a complementary partial area of the test object is in gap-free contact with at least a complementary partial area of the complementary contact element, wherein
   for at least two contact points of the contact element and/or the complementary contact element, which are in contact with the partial area of the test object and/or the complementary partial area of the test object, upon through-radiation by means of electromagnetic radiation that is parallel to the predefined through-radiation direction, an optical path length of the electromagnetic radiation through the holding device, the test object and the complementary holding device is substantially identical; and wherein
   upon having the electromagnetic radiation radiate through the holding device and the test object, the complementary holding device is radiated through as well.

3. The method according to claim 1, comprising the initial step of:
   selecting the contact element and/or the complementary contact element with an optical refractive index that is substantially equal to the optical refractive index of the test object.

4. The method according to claim 1, wherein the electromagnetic radiation is detected by means of an image-forming device.

5. The method according to claim 4, wherein the detected electromagnetic radiation is automatically examined and evaluated by means of an image-processing method.

6. The method according to claim 1, wherein the electromagnetic radiation is homogenous light, and wherein inhomogeneity in the detected electromagnetic radiation is detected by means of the image-processing method.

7. An apparatus for holding at least one test object, comprising
   a holding device with at least one deformable contact element, wherein
   the deformable contact element is arrangeable to accept a test object such that
   at least a partial area of the contact element is in contact with at least a partial area of the test object in substantially gap-free fashion, and
   for at least two contact points of the contact element, which are in contact with the partial area of the test object, upon through-radiation by means of electromagnetic radiation that is parallel to a predefined through-radiation direction, an optical path length of the electromagnetic radiation through the holding device and the test object is substantially identical.

8. The apparatus according to claim 7, comprising a complementary holding device with at least one deformable complementary contact element, wherein the deformable complementary contact element is arrangeable to accept the test object such that at least a complementary partial area of the test object is in contact with at least a complementary partial area of the complementary contact element in substantially gap-free fashion.

9. The apparatus according to claim 7, wherein the deformable contact element and/or the complementary deformable contact element has/have an optical refractive index that is substantially equal to an optical refractive index of the test object.

10. The apparatus according to claim 8, wherein the contact element and the complementary contact element are arrangeable to accept the test object at least partially between the contact element and the complementary contact element.

11. The apparatus according to claim 7, wherein the holding device comprises a base device at which the deformable contact element is arranged, and/or
    wherein the complementary holding device comprises a complementary base device at which the deformable complementary contact element is arranged.

12. The apparatus according to claim 7, wherein the base device and/or the complementary base device has/have plane-parallel surfaces.

13. The apparatus according to claim 7, wherein the contact element and/or the complementary contact element is/are composed of an elastomer.

14. The apparatus according to claim 13, wherein the elastomer is at least partially surrounded by a film.

15. The apparatus according to claim 11, wherein the contact element and/or the complementary contact element is/are composed of a liquid or a gel, which is provided in a bag formed of a film.

16. The apparatus according to claim 7, comprising a detection device configured to detect electromagnetic radiation after at least partial through-radiation of the holding device and at least partial through-radiation of the test object.

17. The apparatus according to claim 7, comprising an evaluating device configured to evaluate the detected electromagnetic radiation.

18. The apparatus according to claim 7, comprising a display device configured to display the detected electromagnetic radiation.

19. The method according to claim 2, comprising the initial step of:
   selecting the contact element and/or the complementary contact element with an optical refractive index that is substantially equal to the optical refractive index of the test object.

20. The apparatus according to claim 8, wherein the deformable contact
   element and/or the complementary deformable contact element has/have an optical refractive index that is substantially equal to an optical refractive index of the test object.

* * * * *